(12) United States Patent
Chedister (10) Patent No.: US 6,310,471 B1
(45) Date of Patent: Oct. 30, 2001

(54) CARD WITH MAGNETIC STRIPE AND METHOD FOR TESTING MAGNETIC INSPECTION PARTICLE FLUID

(75) Inventor: William C. Chedister, Geneva, IL (US)

(73) Assignee: Circle Systems, Inc., Hinckley, IL (US)

( * ) Notice: Subject to any disclaimer, the term of this patent is extended or adjusted under 35 U.S.C. 154(b) by 0 days.

(21) Appl. No.: 09/391,097

(22) Filed: Sep. 7, 1999

(51) Int. Cl.$^7$ .................................................. G01N 27/74
(52) U.S. Cl. ........................ 324/204; 324/232; 324/214
(58) Field of Search .................................. 324/204, 214, 324/216, 228, 232, 672; 29/558; 235/493, 449; 428/457, 900; 340/551, 572, 631; 73/53.05, 53.07, 61.42, 61.72

(56) References Cited

U.S. PATENT DOCUMENTS

| | | |
|---|---|---|
| 3,320,523 | 5/1967 | Trimble ................................ 324/214 |
| 3,755,730 | 8/1973 | Vogelgesang ........................ 382/104 |
| 4,281,043 * | 7/1981 | Deffeyes .............................. 428/457 |
| 4,909,081 | 3/1990 | Kulczyk et al. ....................... 73/597 |
| 5,055,783 * | 10/1991 | Jones et al. ........................... 324/216 |
| 5,602,527 * | 2/1997 | Suenaga ................................ 340/551 |
| 5,698,839 * | 12/1997 | Jagielinski et al. .................. 235/493 |

* cited by examiner

*Primary Examiner*—Safet Metjahic
*Assistant Examiner*—Subhash Zaveri
(74) *Attorney, Agent, or Firm*—Mathew R. P. Perrone, Jr.

(57) ABSTRACT

A magnetic stripe card provides a quantitative tool for the measurement of magnetic sensitivity for fine-grained iron, iron oxide or other ferro-magnetic powders, that may be used for magnetic particle inspection and other purposes. The magnetic stripe card is encoded to establish distinct areas on the magnetic stripe. Each distinct area has a specific magnetic gradient. Ferro-magnetic powders are attracted to the gradient in proportion to the value of the gradient. A higher gradient more strongly attracts the powder. A determination of the sensitivity of the powder can be ascertained by observing the gradient with the lowest value to which the powder is attracted.

20 Claims, 3 Drawing Sheets

CARD WITH MAGNETIC STRIPE AND METHOD FOR TESTING MAGNETIC INSPECTION PARTICLE FLUID

This invention relates to a device and method for testing magnetic inspection particle materials and more particularly to a device having at least one predetermined magnetic stripe situated thereon to receive a magnetic inspection particle suspension in order to provide a method for determining the effectiveness of the particle suspension or system for use in testing.

BACKGROUND OF THE INVENTION

It is well known in the art that magnetic inspection particle systems are useful and important in industrial applications. The basic application of this system is for non-destructive testing of an item. This importance is clearly set forth in U.S. Pat. No. 4,812,249 relating to a test system by Isabelle Y. Duminy-Kovarik, incorporated herein by reference.

A major problem with the magnetic inspection particle system is a testing of the materials and particles themselves for their effectiveness. This test for effectiveness is critical. As parts are inserted into the suspension, and tested, the testing suspension of particles will lose some of its effectiveness. It is very critical to have the suspension be effective and be able to easily determine the effectiveness of that suspension by a simple test, in order to have each part tested efficiently.

A suspension for the purposes herein is deemed to include wet method materials borne in conditioned water or kerosene-type liquid, and dry-method materials applied directly to the test surface.

This action is critical because of the expensive nature of the suspension, and the expensive parts which are being tested. It is hypercritical that these parts be tested efficiently and effectively with an effective suspension. If such efficient or effective testing is not achieved, or if the suspension is not known to have failed or been found deficient in its effectiveness, a detective part may receive a false approval and be used in a dangerously unsuitable manner. This defective part can eventually lead to a failure of a system in which it is used.

In order to compensate for this depletion of the magnetic inspection particle fluid during a series of tests on various parts, it is known to use a piece or part with a known crack in it for testing purposes. This process or testing mechanism is difficult to reproduce from factory to factory or establishment to establishment because no two cracks are the same. Thus, a part with a predetermined crack may not be the same as a part with predetermined crack in another location. In this fashion, it is impossible to use this test to have an accurately reproducible test at various locations.

There is also a settling tube or bulb test. However, the settling tube test merely shows the number of particles in the suspension. It does not show the effectiveness of the particles or the brightness of the particles or the sensitivity of the particles. The settling bulb test merely shows the number of particles in the suspension. A repeatedly used fluid can lose brightness and sensitivity. The settling bulb test is also effected by dirt, scale and metal particles from the part itself being tested. The settling bulb test thus suffers from a number of inaccuracies, especially regarding actual particle performance.

Another test for use a magnetic inspection particle fluid is a ring test. This device is accomplished by a ketos ring or Tiede MTU#3 ring. These rings suffer from a similar problem in that the ring itself is not consistently reproducible. This factor greatly interferes with the desirability of providing the same test to the same fluid at a number of different sites.

Ketos Ring Discussion

Similar testing patterns are important to determine the similar quality of the parts. The ketos ring is made of tool steel, and is a flat disc like device having a plurality of apertures drilled at various radial distances from the circumference thereof. The degree of magnetization of the ring, combined with the differing qualities of the steel and the spacing of the apertures, can have an adverse effect on the test mechanism. The defects in the ketos ring are well discussed in a paper presented by Donald Hagemaier at the 1992 ATA NDT Forum in Cincinnati, Ohio, which paper is incorporated herein by reference.

The Ketos ring is a tool that is most commonly used as grading device for evaluating the sensitivity of MPI materials. It is described most accurately by Aerospace Standard AS5282. The Ketos ring is actually a disk made of SAE J438 steel, which is manufactured with properties as described within AS5282. The disk contains a centrally located aperture, which receives a conductive copper bar. Various currents of electricity are passed through that centrally located conductive copper bar in a controlled manner. These currents ultimately generate varying magnetic fields and gradients associated with each of several small apertures drilled at varying distances inside the circumference of the ring. The small apertures are placed in such a manner that their associated fields and gradients become weaker as they are further from the circumference.

Magnetic particles can be applied to the circumference of the ring as a current is passed through the central conductor. Particles are graded by the number of apertures that can be detected by displaying a formation of particles at the circumference above the aperture at given amperage. A more sensitive powder will show more apertures than a less sensitive powder.

AS5282 describes a procedure for evaluating the Ketos ring performance by means of a magnetic field measuring device that sense the residual fields associated with the apertures after the ring has been exposed to current of 1500 amps of direct current. While this use of residual fields may suffice for evaluating rings it does not represent the gradients used to grade particles as generated by the various currents.

The Ketos ring has been accepted as the standard tool for measuring particle performance for many years. Much of this acceptance has probably been due to the fact that, despite a variety of troublesome issues surrounding the ring, a suitable replacement had not been developed. The issuance of AS5282 in 1997 has provided a standardized means of evaluation and grading rings but many inherent (and quite possibly problematic) issues remain:

- AS5282 evaluates the Ketos ring in a residual state of magnetization. The correlation between the residual state and the active magnetic state at which the ring is used has not been firmly established.
- The values of the magnetic fields and gradients associated with the respective apertures in the active magnetic state are not described.
- Consistency of the magnetic properties of the steel from which the rings are made.
- Many rings in use in industry have probably not been certified to AS5282.

A ring is only compared to itself in the residual state. Consistency between rings is not addressed.

AS5282 calls out that 3-phase, full-wave, rectified alternating current be used for ketos ring evaluation. This type of current may not always be readily available, depending on the type of equipment used by a given inspector.

The magnetizing equipment providing the current must be in proper calibration. The equipment, and even the process of equipment calibration, can be subject to error and tolerance that can affect the performance of the Ketos ring.

The complete cleaning and processing of the ring can be a time-consuming procedure.

The cleanliness of the ring surface can affect observations.

MPI is almost always used as strictly a surface inspection technique of nondestructive testing (NDT). The Ketos ring requires the evaluation of subsurface discontinuities. Interpretation of these discontinuities, especially as they are further in from the circumference, can be very subjective and subject to inspector interpretation.

The position of the ring on its central conductor bar can affect the observations.

The direction and amount of flow of particles over the ring can affect the observations.

The ability or inability of wet-method solutions to flow evenly over the surface of the ring can affect the observations.

Tiede MTU #3 Block

This device is a permanently magnetized steel disk that has been polished and heat-treated to form a pattern of various sized cracks on its flat surfaces. However, this Tiede block has a number problems. The permanent magnetization can clearly be affected if the block is dropped or otherwise mishandled. Also, the consistency from block to block cannot be ascertained.

Fluxa Block

The fluxa block is another inaccurate standard device, which can be used to compare MPI materials. The Block has a small permanent magnet encased within a rectangular prism. The prism is comprised of two steel pieces and one brass piece, assembled such that the meeting surface of the steel pieces acts as a "discontinuity", which can be incremented to demonstrate particle sensitivity. While this device allows a quantitative observation to be made it is subject to the same difficulties of the Tiede MTU #2 Block.

Settling Tube

The settling tube is another time-honored method for wet-method MPI bath evaluation. The use of the tube is generally required in virtually all military and industrial specifications. The value of the tube lies in its use for observing the amount of particle material in a specified volume of bath. Also, it can be used to observe either solid or liquid contaminants that may have been introduced into the bath. As far as actually evaluating the particle performance, the settling tube is not especially effective because for many reasons. Use thereof requires that it be left undisturbed for at least thirty minutes before observations can be made. Also, discoloration in the fluid above settled particles may not necessarily mean that the performance of the bath has been diminished. The significance of the test is somewhat diminished because observation of the fluid in the tube is no longer required in ASTM E-1444 and many other procedural specifications. The observations allowed by this test do not, in themselves, fully describe the performance of the particles. A useable bath, as demonstrated by more meaningful tests, may not meet the requirements of the settling tube test. Interpretation of the settling volume can be very subjective. Supplemental tests are required even if the settling tube test yields acceptable findings.

Shims

Reference Standard Notched Shims ("shims") are in use and are especially valuable in establishing the proper magnetic fields necessary to suitably inspect a given object with MPI. The shims are thin pieces of low carbon steel that contain artificial flaws produced by a photochemical method. The manufacture and use of shims is discussed in the conventional Aerospace standard under AS 5371. Another device referred to as the Burma Castrol Strip is constructed in a different manner but serves the same purpose. While shims can be effective in determination of magnetization levels and field direction their use as a evaluation of MPI materials is limited for the following reasons.

Shims must be securely and consistently attached to the surface of the object being magnetized.

The observations can be affected by any matter on the surface of the shim, including even any dirt or oil film from the finger of the person applying the shim to the object.

The type and direction of magnetizing current affects the observations.

The geometric complexity of the part to which the shim is attached can be significant.

Indications can be subject to the methodology of application of the particle bath and can be easily washed away.

Pieces with Known Defects

The use of pieces with known defects is an accepted means of MPI system quality control. These defects can be either naturally occurring or manufactured by a process such as electronic discharge machining (EDM). Similar to the shims these pieces may be effective as a system quality control device but are not necessarily effective as a particle evaluation device:

Detection of defects is subject to proper strength and orientation of the applied magnetic field.

Observation of defects serves as a "go/no go" statement rather than a description of particle performance.

Likewise, the Tiede MTU#3 ring is formed to exhibit a pattern of cracks. It is difficult to get a reproducible pattern of cracks to form from ring to ring. Thus, the Tiede MTU#3 ring is not a consistent test of the suspension.

Two of the main problems with the Tiede MTU#3 ring and the ketos ring is that each may be improperly magnetized, and that there is no reliable method for determining the proper magnetization of either of those rings. Thus, tests of the fluid with those types of rings may be inaccurate and depend on the unpredictable quality of the individual ring.

The rings inability to consistently magnetize fails to provide for a repeatable and reproducible test system. The use of single phase versus three phase current is a major problem in achieving magnetism. Furthermore, the issue of alternating current versus direct current is a major problem with the reproducibility for both of the rings.

The ketos ring and the Tiede ring fail to provide an absolute standard, due to unpredictable magnetization. There is also a major logic problem. This logic problem of the ketos ring is based on the fact that first, the particles in a suspension are used to grade a ring, and then that ring is used to grade the suspension of particles.

SUMMARY OF THE INVENTION

Therefore, among the many objectives of this invention is to provide a device for testing a magnetic inspection particle suspension with repeated accuracy.

A further objective of this invention is to provide a card having a magnetic stripe thereon to determine effectiveness of a magnetic inspection particle fluid suspension.

A still further objective of this invention is to provide a device for efficiently determining the effectiveness of the magnetic inspection fluid suspension.

Yet a further objective of this invention is to provide a device for properly testing a magnetic inspection suspension, which provides an alternative for a ketos ring.

Also an objective of this invention is to provide a device for testing magnetic inspection suspension, which provides an alternative for a Tiede ring.

Another objective of this invention is to provide a device for testing a magnetic inspection fluid, which provides an alternative for a settling tube.

Yet another objective of this invention is to provide a device for testing magnetic inspection suspension, which shows brightness of the fluid suspension.

Still another objective of this invention is to provide a device for testing magnetic inspection suspension, which shows sensitivity of the fluid suspension.

A further objective of this invention is to provide a method using card with at least one magnetic stripe thereon to determine effectiveness of a magnetic suspension.

A still further objective of this invention is to provide a method for efficiently determining the efficiency of the magnetic suspension.

Yet a further objective of this invention is to provide a method for properly testing a magnetic inspection suspension, which provides an alternative for a ketos ring.

Also an objective of this invention is to provide a method for testing magnetic inspection suspension, which provides an alternative for a Tiede ring.

Another objective of this invention is to provide a method for testing a magnetic inspection suspension, which provides an alternative for a settling tube.

Yet another objective of this invention is to provide a method for testing magnetic inspection suspension, which shows brightness of the fluid.

Still another objective of this invention is to provide a method for testing magnetic inspection suspension, which shows sensitivity of the fluid.

A further objective of this invention is to provide a method using an absolute standard for testing a magnetic particle suspension.

A still further objective of this invention is to provide a method for logically determining the efficiency of a magnetic particle suspension.

These and other objectives of the invention (which other objectives become clear by consideration of the specification, claims and drawings as a whole) are met by providing a card with a magnetic stripe thereon, having a predetermined pattern applied to the stripe, with the pattern being suitable to determine the effectiveness of the magnetic inspection suspension.

BRIEF DESCRIPTION OF DRAWINGS

Throughout the figures of the drawings, where the same part appears in more than one figure of the drawings, the same number is applied thereto.

DESCRIPTION OF THE PREFERRED EMBODIMENTS

A device for testing a magnetic particle suspension is a card with at least one magnetizable stripe. The card with a magnetized stripe can provide a test of a magnetic inspection particle material due various magnetic strengths along the magnetizable stripe. The magnetization or encoding of the stripe is easily reproducible and duplicatable. With this stripe, a suitable magnetic inspection particle material will produce a certain pattern on the magnetic stripe. All that is required is to some way apply the magnetic inspection particle material to the card and evaluate the pattern achieved.

The stripe may additionally be coated with any clear nonmagnetizable coating to protect the stripe and permit successive uses. A typical coating is polyethylene, polypropylene or similar polymeric coatings. The card with a lower magnetic gradient has more discrimination as to the particles. That is to say, the card with the lower coercivity is more easily affected by strong magnetic fields. An identical stripe is created easily by the card magnetic encoding magnetization process, which is carried out in a standard fashion. Preferably the card is colored or non-white, as opposed to white, in order to avoid reflection of ultraviolet illumination. It is also permitted to create several tracks on one stripe on the card in order to achieve the desired pattern.

The advantage of the magnetic stripe card when compared to the ketos ring or the Tiede ring is that the card requires no magnetization or demagnetization. It has no moving parts and requires no power source. The reliable duplication or perfection of the stripe on the first card or a different card for the testing provides for a repeatable and reproducible test system. The use of single phase versus three phase current is not an issue with the card, whereas it is a major problem with the rings. Furthermore, issue of alternating current versus direct current is not an issue as it is in either of the rings.

The device is also fail-safe. If the magnetic pattern of the stripe is disturbed, it will not display an acceptable reading. Thus, is almost impossible to get an improper reading. The determination of the gradients can be calculated in a qualitative fashion. This permits more accurate testing. The magnetic properties of the stripe can be verified. The card is portable and inexpensive. Unlike the ketos ring and the Tiede ring, the magnetic stripe card establishes an absolute standard.

I. Determination of Magnetic Gradients for Type C Magnetic Stripe Card

Magnetic gradients are established on the magnetic stripe of a card when the stripe is encoded with a typical alternating current (AC) encoding coil. Simply stated, the stripe is passed under the encoding coil as an AC current flows through the coil. The coil generates a reversing magnetic field proportional to the current. As the stripe passes the coil the domains of the small magnetic elements in the stripe are aligned by the polarity of the magnetic field. The directions of the domains are reversed as effected by the reversing magnetic field. The rate of the card motion and the frequency of the current determine the distance between the domain reversals. The increasing or decreasing the current flowing through the coil can control the intensity of the magnetic field.

Figure 10:
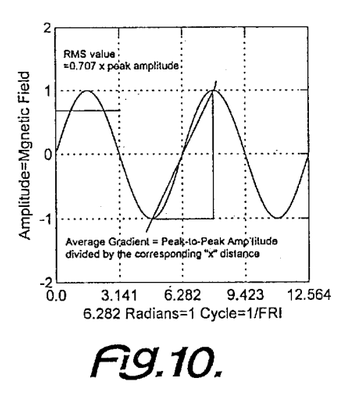
FIG. 10 depicts a graph of in sinusoidal form of the encoding process, showing the magnetic field may alternatively be considered the root mean square of the peak value.

Magnetic particles, which in this case are actually small bits of high-permeability/low retentivity iron and/or iron oxide which may or may not be pigmented or colored, are attracted not to the magnetic field of the stripe but to the magnetic gradient. The magnetic gradient is actually the change in magnetic field over distance. In the case of the magnetic stripe the gradient is determined by comparing the magnetic field (that is, amplitude of the wave) to the distance between reversals (that is, the period). At a given point the gradient can be mathematically considered to be the slope of the line tangent to the sine wave at that point, or, the derivative of the sine at that point. An average gradient can be the maximum distance between the highest and lowest points of the wave divided by the corresponding distance between those points along the x-axis, which will be one-half of the period. At a given point, the gradient can be mathematically considered to be the slope of the line tangent to the sine wave at that point, or the derivative of the sine at that point. Because of the sinusoidal form of the encoding process, the magnetic field may alternatively be considered the root mean square of the peak value (FIG. 10).

Additionally, the logic problem of the ketos ring is based on the fact that the particles are used to grade a ring and the ring is used to grade particles. Thus the card is not only more easily used, the test results are much more reliable. In this fashion, great advantages are be achieved.

The magnetic striped cards can assist in the evaluation of magnetic particle inspection materials. Each card is usable in water bath or oil bath suspensions and may be used with recirculating units, aerosol cans, or portable spraying devices. Dry method materials may also be evaluated with these cards. The magnetic stripe of the type A and type B cards contain a code that attracts particles in a unique pattern of fine lines across the length of the stripe.

This code pattern contains stripes that appear wide but are actually composed of many closely spaced indications. The material is simply applied over the magnetic stripe. The magnetic encoding of the stripe within a certain desired range achieves the desired results. The clarity of the indication on the stripe illustrates the quality of the magnetic inspection particle suspension. As the card is wiped with a soft cloth, it may be reused.

The type A card is used for the high coercivity applications. Generally speaking the type A card has an oersted capacity of about 3,000 to about 4,000. More preferably the oersted capacity is about 3,300 to about 3,900. Most preferably the oersted capacity of the type A card is about 3,500 to about 3,800 oersteds.

In a similar fashion, the type B card has a lower oersted capacity. The type B card preferably has a range of about 100 to about 500 oersteds. More preferably, the type B card has a range of about 150 to about 400 oersteds. Most preferably, the type B card has a range of about 250 to about 350 oersteds.

A method of specifically calculating the value of the gradient can be developed based on the magnetic properties of the stripe material and characteristics of the encoding process. Significant magnetic properties include the coercivity and hysteresis of the stripe material. Important characteristics of the encoding process include the amount of encoding current (that is, "write" current), the frequency of the current and the rate of motion of the magnetic stripe card as it passes the encoding coil.

Coercivity describes the magnetic field required to actually effect the direction of magnetic orientation within the stripe material. A material with high coercivity requires a stronger magnetic field to orient the particles than does lower coereivity material. Coercivity also describes the minimum threshold of magnetic field required to cause an arrangement or re-arrangement of magnetic orientation. Higher coercivity materials are less prone to magnetic erasure.

Hysteresis describes the response of ferro-magnetic material to an applied magnetic force. Ferro-magnetic materials can become "saturated". When saturation occurs the magnetic fields within the material will no longer change or respond to increased magnetic force and in FIG. 11, which shows-Hysteresis and the B-Terminology definitions.

Figure 12:
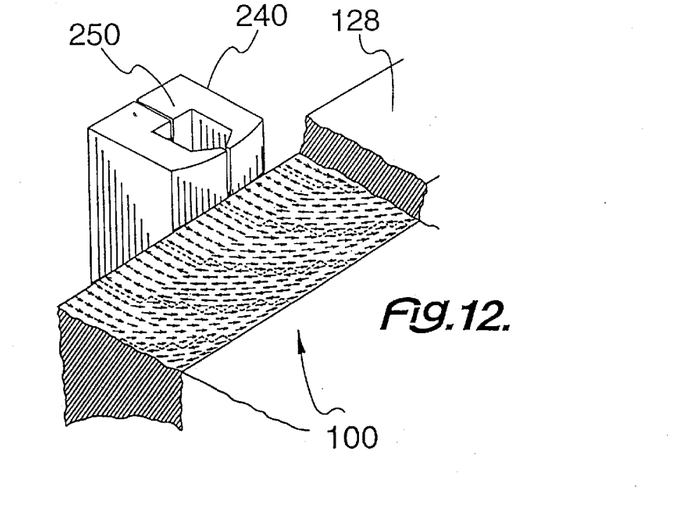
FIG. 12 depicts the encoding device 240 for card 100.

Magnetic gradients are established on the magnetic stripe of a card when the stripe is encoded with a typical alternating current (AC) encoding coil. Simply stated, the stripe is passed under the encoding coil as an AC current flows through the coil. The coil generates a reversing magnetic field proportional to the current. As the stripe passes the coil the domains of the small magnetic elements in the stripe are aligned by the polarity of the magnetic field. The directions of the domains are reversed as effected by the reversing magnetic field. The increasing or decreasing the current flowing through the coil can control the intensity of the magnetic field, as shown with the FIG. 12 and the encoding device therein.

The rate of the card motion and the frequency of the current determine the distance between the domain reversals. The current will typically have a frequency of 60 Hertz, or 60 cycles (reversals) per second. A card moving past the encoder at a rate of one inch per second will thus be encoded with 60 flux reversals per inch (FRI). If the card is moved at 0.25 inch per second, it will be encoded at 240 FRI. The distance (that is period) of the complete cycle in the latter case will be $\frac{1}{240}$ of an inch (0.0042 inch).

A method of specifically calculating the value of the gradient can be developed based on the magnetic properties of the stripe material and characteristics of the encoding process. Significant magnetic properties include the coercivity and hysteresis of the stripe material. Important characteristics of the encoding process include the amount of encoding current (that is "write" current), the frequency of the current and the rate of motion of the magnetic stripe card as it passes the encoding coil.

The reversing magnetic field is, by this method, encoded into the magnetic stripe of the card. The field can be represented by a conventional sine wave, with the amplitude proportional to the magnetic field and the period being the inverse of the (flux) reversals per distance (typically, flux reversals per inch or FRI).

Figure 11:
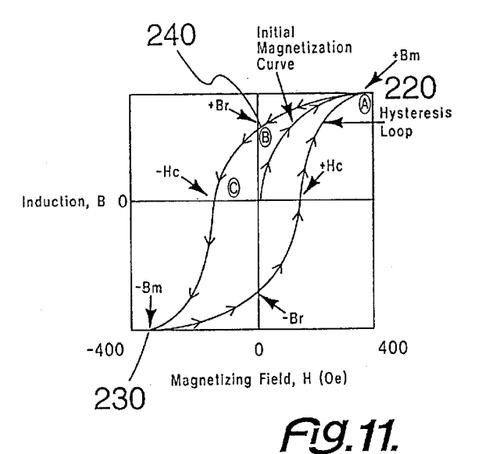
FIG. 11 depicts a graph of the magnetic fields within the material, which will no longer change or respond to increased magnetic force and which shows-Hysteresis and the B-Terminology definitions.

A. Terminology refers to FIG. 11 Hysteresis Curve;

Coercivity ($H_c$): magnetic field required to zero remanent flux (C).

Flux: one line of force (called a Maxwell).

Flux Reversals per inch (FRI): the frequency of the encoding cycle; also, the inverse of the cycle period.

Magnetic field Strength (H): the number of flux lines passing through a unit area perpendicular to the flux.

Magnetic Flux (0): measurement of the number of magnetization or flux lines at a point (Maxwells).

Magnetic Induction (B): the density of the magnetization or flux lines at a point (Gauss).

Oersted (Oe): the number of lines of force or flux passing through an area equal to one cm$^2$.

Period: the distance of one encoding cycle; also, the inverse of the frequency (FRI). For conversion to distance one period equals 2 pi radians. Maximum Magnetic Flux ($0_m$): measurement of the number of magnetization or flux lines at (A).

Maximum Magnetic Induction ($B_m$): the density of the magnetization or flux lines at (A).

Remanent Magnetic Flux ($0_r$): measurement of the number of magnetization or flux lines at (B).

Remanent Magnetic Induction ($B_r$): the density of the magnetization or flux lines at (B).

Root Mean Square (RMS): a means of measuring a periodic quality by averaging the square of a quantity over a period and then taking the square root of the average. The RMS of a sinusoid is the inverse of the square root of 2, or about 0.707 times the peak value.

Saturation: The point of maximum magnetic flux and/or maximum magnetic induction (A).

Squareness: the ratio of $B_r$ to $B_m$; the "ideal" ferromagnetic material has a squareness of 1. Also, the ratio of $0_r/0_m$.

B. Conversion Factors

Distance

1 Inch=1,000 mils=10$^{-6}$ micro inches=25.4 millimeters
1 millimeter=100 microns=0.0394 inches.
1 micron=10$^{-6}$ meters=39.4 micro inches
1 period=6.282 Radians=1/FRI Magnetic Field 1 Oersted=1 Maxwell/cm$^2$=1000/4(pi)A/m=79.6 A/m Magnetic Flux 1 Maxwell=1 flux line/cm$^2$ Magnetic Gradient (1 A/m)/m=1 A/m$^2$ C. Method:

This section describes the process of calculating the magnetic gradient for a given write current and period encoded on the magnetic stripe.

1. Determine the value of Maximum Magnetic Flux Density ($B_m$).

This value is based on typical data provided both by 3M Corporation of Minneapolis, Minn., and Anacomp (former and current manufacturers, respectively, of magnetic stripe material) by the relationships described below (Sections F and G). These relationships are built upon measured values of remnant flux density (Remanence, $0_r$) and Squareness, a ration which can be based on measured data (Section E). Unites are in Oersteds (Oe).

2. Derive the value of the Maximum Signal Amplitude.

A sheet is provided for each Type C MSC when it has been encoded. A value of maximum amplitude for a given zone is dived by the associated percentage of maximum. Units are in millivolts (mV).

3. Set Maximum Magnetic Flux Density as being proportional of Maximum Signal Amplitude.

The Maximum signal Amplitude is directly proportional to Maximum Magnetic Flux Density $B_m$.

4. Determine the percentage of Maximum Signal Amplitude for each zone of a specific Type C MSC.

The percentage of Maximum Amplitude for each zone of a Type C MSC is shown in the table below.

| 1. Zone Source/ Units | 2a. Max Magnetic Induction (3M/Anacomp, Oe) | 2b. Convert Oe to A/m Oe × 79.6 = A/m | 3. Percentage (FIG. 4) | 4. Zone Amplitude A/m | 5a. Period/2 (0.005/2, inches) | 5b. Convert to Meters Inches × 0.0254 | 6. Gradient A/m2 | 7. Gradient (A/m2 × 10E06) |
|---|---|---|---|---|---|---|---|---|
| Zone 1 | 1416 | 112714 | 72 | 81154 | 0.0025 | 0.0000635 | 1278012472 | 1278 |
| Zone 2 | 1416 | 112714 | 68 | 76645 | 0.0025 | 0.0000635 | 1207011780 | 1207 |
| Zone 3 | 1416 | 112714 | 64 | 72137 | 0.0025 | 0.0000635 | 1136011087 | 1136 |
| Zone 4 | 1416 | 112714 | 59 | 66501 | 0.0025 | 0.0000635 | 1047260220 | 1047 |
| Zone 5 | 1416 | 112714 | 54 | 60865 | 0.0025 | 0.0000635 | 958509354 | 959 |
| Zone 6 | 1416 | 112714 | 48 | 54103 | 0.0025 | 0.0000635 | 852008315 | 852 |
| Zone 7 | 1416 | 112714 | 41 | 46213 | 0.0025 | 0.0000635 | 727757102 | 728 |

-continued

| 1. Zone Source/ Units | 2a. Max Magnetic Induction (3M/Anacomp, Oe) | 2b. Convert Oe to A/m Oe × 79.6 = A/m | 3. Percentage (FIG. 4) | 4. Zone Amplitude A/m | 5a. Period/2 (0.005/2, inches) | 5b. Convert to Meters Inches × 0.0254 | 6. Gradient A/m2 | 7. Gradient (A/m2 × 10E06) |
|---|---|---|---|---|---|---|---|---|
| Zone 8 | 1416 | 112714 | 36 | 40577 | 0.0025 | 0.0000635 | 639006236 | 639 |
| Zone 9 | 1416 | 112714 | 27 | 30433 | 0.0025 | 0.0000635 | 479254677 | 479 |
| Zone 10 | 1416 | 112714 | 20 | 22543 | 0.0025 | 0.0000635 | 355003465 | 355 |
| Zone 11 | 1416 | 112714 | 11 | 12398 | 0.0025 | 0.0000635 | 195251906 | 195 |

5. Apply the percentage from Step 4 to the Maximum Magnetic Flux Density to find the Flux Density for each zone.

Multiply the respective percentages by the Maximum Magnetic Flux Density. Units are in Oersteds.
6. Determine the period of Signal Amplitude.

A magnetic stripe card is encoded at a set value of flux reversal per inch (FRI). FRI is a variable that can be controlled and changed. The period for a given FRI is its inverse value (that is: 1/FRI). Units are in inches.
7. Divide the value from Step 5 (Flux Density by one-half (50%) of the Step 6 period to determine the Average Magnetic Gradient for each zone.

Magnetic Gradients are expressed as the Change in Magnetic Field (dH) versus the change in Distance (dx). (dH) is the peak-to-peak amplitude of the Flux Density for each zone; dx is the distance along the x-axis from peak-to-peak. At this point the units are in Oersteds/inch. A more conventional unit for gradients is Amperes per meter per meter (A/m$^2$). The conversion factors are:

1 Oersted=1000/4 microAmperes/Meter

1 Inch=0.0254 Meters.

Therefore, Oersteds/inch×3133=A/m$^2$, This shall be divided by 1000 to get to units of kA/m$^2$.
D. Measured Encoding Data:

Squareness is a ratio of remanent magnetic induction 220 on FIG. 11 to maximum magnetic induction 230 on FIG. 11. These values were measured to be 31.1 EMU and 44.3 EMU, respectively. EMU's are Electromagnetic Mass Units. The use of these units are not important here; the significance for these values is that they describe the relationship between the remanent and maximum values of magnetic induction.

$B_r$=31.3 EMU (measured)

$B_m$=44.3 EMU (measured)

Squareness=$B_r/B_m$=31.3/44.3=0.706

E. 3M Methodology:

3M Corporation used to be involved with the manufacture of magnetic stripe materials but is no longer involved with these materials. 3M personnel did provide the following relationship to determine Retentivity ($B_r$) based on their typical values:

Retentivity ($B_r$)=(Remanence ($0_r$)×630×1000)/Stripe Thickness (0r)=0.85 Maxwells (typical)

Stripe Thickness=550 u-inches (typical)

Retentivity ($B_r$)=(0.85×630×1000)/550=974 Oe Maximum Flux Density ($B_m$)=$B_r$/Squareness =974/0.706 =1380 Oe F. Anacomp Methodology:

Anacomp Corporation is currently involved with the manufacture of MSC materials. Anacomp provided the following relationship to determine the retentivity of MSC material:

$B_r = O_r/$(Stripe Thickness) × 0.0000129

$O_r$ −= 5.7 Maxwells (typical for a 2.0 inch square sample)

$B_r$ = (5.7)/(420 × 0.0000129)
    = 1052 Oe $(B_m) = B_r/$Squareness
    = 1052/0.706
    = 1490 Oe G. Application of Method and Data to Type C MSC #0001 (Summary of above chart).
1. $B_r$=974 Oe from 3M and 1052 from Anacomp. Both of these are typical values. For the purpose of this example $B_r$=1000 Oe. The squareness for a Type C MSC is measured to be 31.4/44.3=0.706.
2. $B_m$=$B_r$/-/706=1416 Oe.
3. The overall amplitude average in microvolts (1425.2 mV) and overall amplitude average percentage (45.97%) at the bottom of the data field. Dividing the amplitude by the percentage, the equation becomes Maximum amplitude= 1425.2/0/4597=3100 mV.
4. Assuming that 3100 mV is directly proportional to 1416 Oe, the percentages may be validly applied to either figure.
5. The percentages from each of the zones are calculated in the standard fashion.
6. Type C MSC #0001 is encoded at a rate of 200 FRI. The period is the inverse of FTI; in this case 1/200=0.005 inches per period. This value is divided by two to find the average gradient.
7. the Average Magnetic Gradient for each zone is calculated and displayed on the table below. (Column 6 Gradient= Column 4 zone Amplitude/Column 5 Period/2). (Column 7 Gradient=column 6 Gradient×3133 conversion factor).

I. Comments

A range of gradients is displayed on the table that have been generated by the encoding process described above. The change in gradients from zone-to-zone is due only to the change in current flowed through the encoding coil. These gradients can also be effected by changing the rate of flux reversals by either changing the frequency of the current of the rate of which the card is passed by the coil. With a constant frequency the period will be increased, thus decreasing the gradient, by increasing the rate of motion of the card past the coil. Conversely, if the card were moved slower past the coil the period will be decreased with resulting higher gradients. The amplitude of the magnetic induction can range from below ten (10%) percent up to 100% of the maximum magnetic induction (Point A on the Hysteresis curve). In other words, the peak-to-peak values can range from less than 10,000 A/m to over 100,000 A/m.

Also, the encoding FRI (flux reversals per inch) can range from over 400 to less than 20. The corresponding period thus, respectively, becomes less than 0.0025 inch to over 0.05 inch.

Certainly with a magnetic stripe card there is caution of how well the encoded pattern withstands the course of time and possible accidental erasure. Low-coercivity materials (rated about 300 Oersteds) are not likely affected by stray magnetic fields, and high-coercivity materials (about 3,000 Oe) are even less affected. Time is in itself not a factor towards the degradation of an encoded pattern.

The cards discussed herein are intended for use around strong magnetizing equipment. Since magnetic fields drop drastically as distance from the magnetic field source increases, there will probably still be no effect on the cards. The cards are in effect a "fail-safe" type of device. That is, if the encoding were to be disturbed, the card will not display any pattern when MPI materials were applied. This lack of signal will stop a competent inspector from proceeding until further evaluation of the MPI materials is conducted. If there were any questions about a particular card, that card can be simply and thoroughly evaluated by passing it through encoding equipment that originally encoded and documented it, for example, the equipment depicted in FIG. 12.

IV. Material Test Devices

The designed purpose of the Type C MSC is to provide an instant evaluation of the particle material or bath used in the process of magnetic particle inspection. There are several devices currently in use that can function effectively but have their unique drawbacks. The most commonly used devices are listed below, along with a brief description of their operation and performance.

Type C Magnetic Stripe Card

The encoded magnetic stripe card (MSC) is very attractive as a tool for evaluation of MPI materials. The advantages of the use of the MSC include.

The testing process is very simple, because the as-used MPI material is poured over the magnetic stripe of the card and observations are noted.

The test is instantaneous.

No equipment preparation is required.

The encoded card requires no magnetization prior to use.

Documentation of the particle performance on the card is easily accomplished.

After use, the card is easily wiped off and stored.

The card is not de-magnetized after use.

The encoding process is repeatable.

The encoding process is reproducible.

The card provides an absolute, quantitative standard.

The card is fail-safe; A card that has become accidentally erased will not display any discernible particle pattern. The material being evaluated shall not be allowed for use until found acceptable by another card or test.

The smooth surface of the card allows for an observation of the water break test for water-based MPI solutions.

Particle formations on the stripe are very representative of deductibility of surface cracks (as compared to subsurface cracks).

The card is easily stored.

The card is unbreakable and can be used and re-used for many years.

The card is completely independent of the current type and waveform of MPI magnetizing equipment.

The card is not subject to MPI magnetizing equipment calibration.

The card may be re-evaluated to verify its encoded properties at any time.

The value of the magnetic gradient encoded on the card can be controlled by the encoding amperage.

The value of the magnetic gradient encoded on the card can be controlled be the encoding frequency (FRI).

The indication of the magnetic particle inspection, which is applied to the card, may be dried and lifted off the card with a transparent tape. The tape may then be attached to another substrate for separate evaluation and/or storage of the test results.

The magnetic stripe consists of magnetic material in a binder system that is coated onto a backing material. The stripe on magnetic stripe cards is itself coated again to prevent mechanical wear on the stripe from the magnetic particle materials being evaluated.

The magnetic stripe particles dispersed in the binder system are the important memory elements in the overall stripe construction. There are literally millions of these particles in the stripe and when the stripe is encoded each particle may be considered as small magnet with a north-south polarity. The polarities are set in specific directions by the encoding process and their resulting magnetic fields will be visualized with the use of inspection particles.

These individual magnets retain their encoded magnetic strength and polarity unless acted upon by some significant outside force. The three most notable forces are heat, external magnetic fields and radiation. It is unlikely that the cards are at all affected in the course of normal inspection activity.

The heat required to destroy the magnetism in a magnetic material is known as its curie temperature. The curie temperatures of the materials used as the magnetic stripes range from 110° Centigrade (250° F.) and higher. The other materials involved in the card construction are rendered useless before the temperature is reached. Unless exposed to a fire, there is little danger of failure of the magnetic stripe due to temperature.

Coercivity, expressed in oersteds, is a measure of the magnetic field strength required to affect erasure or polarity reversal in a magnetic material. An external magnetic field 50 oersteds or less will have very little erasing effect on any stripe with a coercivity greater than 250 oersteds. The Type A high-coercivity card most preferably has a coercivity of 3600 oersteds, and the Type B most preferably has a low-coercivity level of 300 oersteds. Because the strength of a magnetic field falls off by the square of the distance from the source, the mere spacing between the stripe and the magnetic field source offers considerable protection.

Examples of some field strengths for reference purposes are as follows. For the English system, earth's magnetic field is about 0.6 Oe; the field strength on the case of an electric drill is about 10 Oe; the field about three inches away from a 1500 Oe degausser drops to about 50 Oe. For the metric system, the field strength directly on the case of an electric hand drill is about 10.0 oersteds. The field strength about 7.5 centimeters away from a 1500 oersted bulk degausser is under about 50.0 oersteds. None of these values will be likely to affect the encoded pattern. The earth's magnetic field is about 0.6 oersteds.

Based on tests that purposely expose magnetically precoded materials to microwave radiation and x-rays, the intensity levels below those that adversely affect a human being will have no adverse effects on the recorded signals. Also, cards are evaluated after extended exposure to an approved kerosene-type carrier vehicle and a conditioned water bath typically used for magnetic particle inspection. Neither fluid causes any detrimental effect on the magnetic properties of the cards.

Usually particle refers to a finely divided power of highly permeable ferromagnetic iron/oxide which can be readily attracted to a magnetic field. Fluid refers to a liquid for wet-method magnetic particle inspection used to transfer or carry the particles over the inspection surface. The fluid is typically a high-flashpoint kerosene or water containing conditioning agents.

Suspension refers to the combination of particles and the fluid. The particles are, in effect, suspended in the fluid. Suspension can be broadly defined to include dry-method particles which are applied directly to an inspection surface without the use of a fluid.

Figure 1:
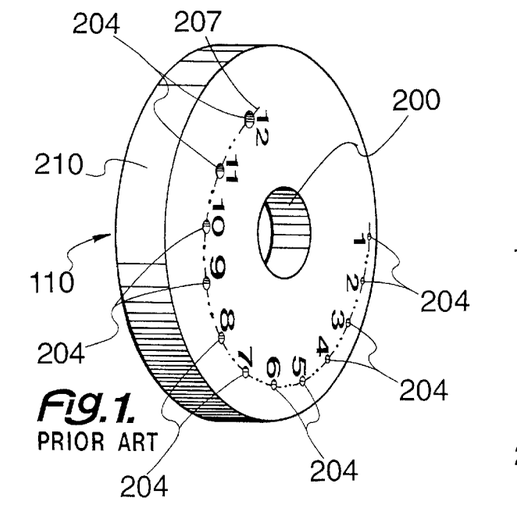
FIG. 1 depicts a front perspective view of the prior art ketos ring 110.
Figure 2:
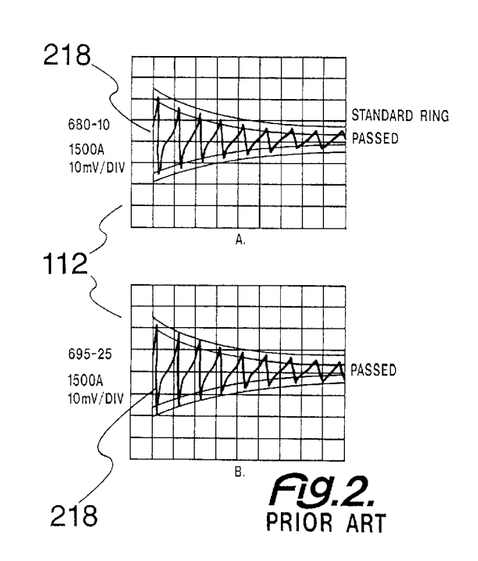
FIG. 2 depicts a pass test pattern 112 for ketos ring 110.

In FIG. 1, the ketos ring 110 is depicted. Ketos ring 110 includes a central aperture 200. Around the edge is an indentation arc 202. Indentation arc 202 has twelve cylindrical indentations 204 forming the arc 202. Each cylindrical indentation 204 has a different spacing from ring edge 210 in order to provide the desired test FIG. 2 shows tests of the ketos ring 110 wherein the ring 110 has passed. In the test, the ring 110 has an electrical current run therethrough, and the flow of the current through the ring provides a readout in the form of toothed symbols 212 indicated in Section A and Section B of FIG. 2. Basically, as the cylindrical indentation 202 is closer to the edge 210, the left end 214 of the tooth symbols 212 graph narrows and the peaks become progressively lower at right end 216. As the cylindrical indentation 202 is further away from the edge, the right end 216 of the toothed symbols 212 graph appears, thereby forming passed tooth graph 218.

Figure 3:
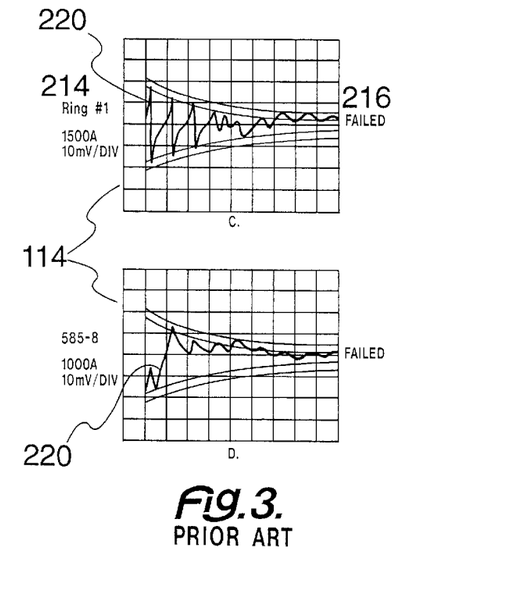
FIG. 3 depicts a fail test pattern 114 for ketos ring 110.

In FIG. 3, the failed tooth graph 220 is not as distinct in any way, shape or form as passed tooth graph 218. As such, failed tooth graph 220 indicates, as the current passes therethrough, that the ketos ring 110 has failed. The device 100 using card 120 of this invention overcomes those problems and permits a simpler testing of the material used for magnetic particle suspension testing of parts.

Figure 4:
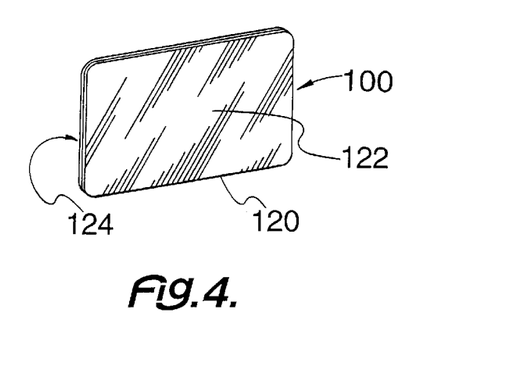
FIG. 4 depicts a front perspective view of magnetic inspection suspension device 100 of this invention.

Referring now to FIG. 3 and FIG. 4, magnetic inspection suspension device 100 of this invention appears similar to a standard credit card. Magnetic inspection suspension device 100 includes a card 120. Card 120 is generally made of a nonmagnetic and a nonmagnetizable material, such as a synthetic resin, polymer, copolymer or plastic.

The front side 122 of card 120 may have any suitable information applied thereto by printing or other suitable fashion. Card 120 is a thin, flat piece of material. Rear side 124 of card 120 includes stripe 126. Stripe 126 is capable of retaining a magnetic charge to determine the effectiveness of the magnetic suspension.

Figure 5:
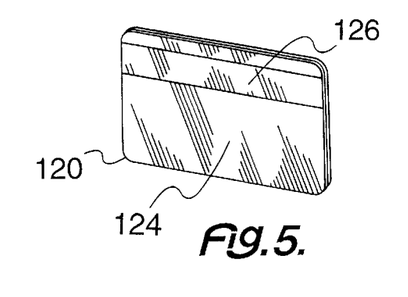
FIG. 5 depicts a rear perspective view of magnetic inspection suspension device 100 of this invention.

In FIG. 5, it may be seen that more than one stripe 126 may be applied to the rear side 124 of card 120. This permits the same suspension to undergo a number of different tests with one card 120.

Figure 6:
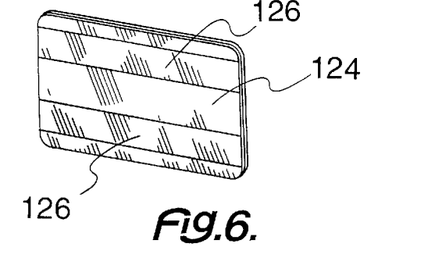
FIG. 6 depicts a rear perspective view of magnetic suspension device 100 of this invention, with card 120 having more than one of stripe 126.
Figure 7:
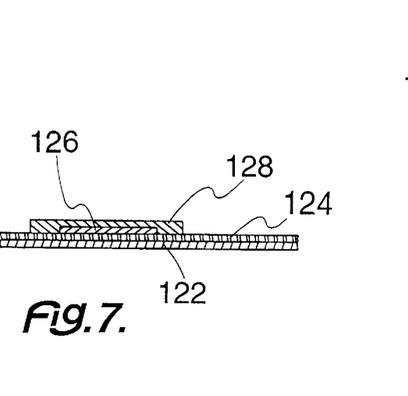
FIG. 7 depicts an edge view of magnetic inspection device 100 of this invention.

By considering FIG. 6 and FIG. 7, the structure of card 120 becomes clear. Card 120 is shown with stripe 126 thereon. Coating 128 can be applied to protect stripe 126.

Figure 8:
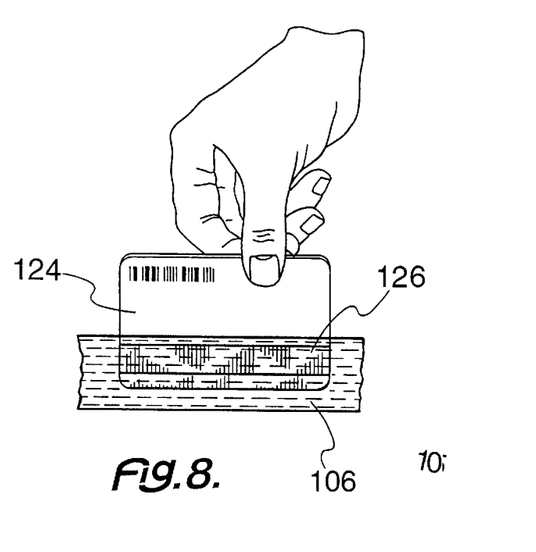
FIG. 8 depicts a view of FIG. 5 with magnetic inspection fluid 106 applied thereto.

FIG. 8 depicts card 120 with magnetic inspection fluid 106 applied thereto for testing purposes. The magnetic pattern of stripe 126 indicates the effectiveness of the fluid 106. The pattern of fluid 106 may be removed by a standard tape or another suitable device. The tape or other suitable device may then be stored for future reference, comparison or any other suitable purpose.

Figure 9:
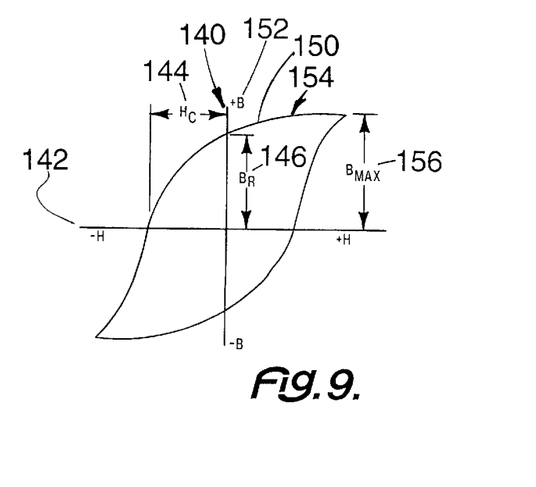
FIG. 9 depicts a graph of magnetic field of the card 120.

With FIG. 9, the magnetic characteristics of stripe 126 are graphically depicted. The magnetizing force (H) 140 forms the X-axis of the graph The magnetic field (B) 142 is depicted on the Y-axis. Magnetizing force (H) 140 is the force used to establish the magnetic field, which in turn is measured in oersteds or amperes/meter (SI), where 1 oersted equals 79.6 A/M.

Coercivity ($H_c$) 144 is the magnetic force 140 required to reduce the residual magnetic field ($B^R$) 146 to zero. Remanence 150 relates to magnetic induction or lines of flux, resulting from the application of the magnetic force 140. Remanence 150 is measured in Maxwells or Webers (SI), where 1 weber=$10^8$ maxwells.

Flux Density (B) 152 relates to remanence 150 per unit area, measured in gauss or tesla (SI), where 1 tesla=10,000 gauss=1 weber/square meter. Retentivity 154 of the magnetic field ($B^R$) 146 relates to the property of a material describing the magnetic field remaining following the removal of a saturating magnetic force, measured in gauss or tesla.

Squareness ($B_R/B_{MAX}$) 156 is the ratio of remanence 150 following removal of the magnetic force 140 to remanence 150 at a saturating magnetic force 140. This ratio describes the alignment of individual elements in a magnetic material. A squareness of 1 is ideal, 0.75 to 0.85 is typical.

The following examples are intended to illustrate without unduly limiting the scope of this invention.

EXAMPLE 1

A card with a high coercivity is suitable for testing a magnetic inspection particle materials is obtained having magnetic properties as shown. The card successfully tests a number of fluids.

| Type A - High Coercivity | |
|---|---|
| Coercivity | 3679 ± 1.0% Oersteds |
| Remanence | 0.85 ± 0.6% Maxwells |
| Squareness | 0.84% ± 0.7% |
| Stripe Thickness | 550 Micro-inches (typical) |
| Retentivity | 974 Gauss |

Retentivity = (Remanence x 630 */Stripe Thickness) x 1000
*630 - Aerial Density Constant

EXAMPLE 2

A card with a low coercivity is suitable for testing a magnetic inspection particle materials is obtained having magnetic properties as shown. The card successfully tests a number of fluids.

| Type B - Low Coercivity Batch # 8252 | |
|---|---|
| Coercivity | 292 ± 1.0% Oersteds |
| Remanence | 0.85 Maxwells |
| Squareness | 0.85 |
| Thickness | 550 Micro-inches (typical) |
| Retentivity | 974 Gauss |

Retentivity = (Remanence x 630 */Stripe Thickness) x 1000
*630 - Aerial Density Constant.

This application—taken as a whole with the specification, claims, abstract, and drawings—provides sufficient information for a person having ordinary skill in the art to practice the invention disclosed and claimed herein. Any measures necessary to practice this invention are well within the skill of a person having ordinary skill in this art after that person has made a careful study of this disclosure.

Because of this disclosure and solely because of this disclosure, modification of this method and apparatus can become clear to a person having ordinary skill in this particular art. Such modifications are clearly covered by this disclosure.

What is claimed and sought to be protected by Letters Patent of the United States is:

1. A device for determining effectiveness of a magnetic particle suspension, the device comprising:
    (a) a card having at least one magnetizable stripe thereon;
    (b) a predetermined, magnetized pattern being applied to the at least one magnetizable stripe;
    (c) the predetermined, magnetized pattern being suitable to determine the effectiveness of the magnetic suspension; and
    (d) the predetermined, magnetized pattern providing at least two different magnetic strength areas to the at least one magnetizable stripe.

2. The device of claim 1 further comprising:
    (a) a clear nonmagnetizable coating protecting the at least one magnetizable stripe; and
    (b) the at least one magnetizable stripe being reproducible.

3. The device of claim 2 further comprising:
    (a) the clear nonmagnetizable coating being at least one coating selected from the group consisting of polyethylene, polypropylene, and mixtures thereof; and
    (b) the at least one magnetizable stripe having a low magnetic gradient in order to provide improved discrimination as to the magnetic particle suspension.

4. The device of claim 3 further comprising:
    (a) the at least one magnetizable stripe being duplicatable in order to provide an improved, repeatable, and reproducible test system; and
    (b) the device failing to display a reading upon loss of magnetism;
    (c) the at least one magnetizable stripe having calculatable gradients in order to provide accurate testing;
    (d) the at least one magnetizable stripe having verifiable properties; and
    (e) the at least one magnetizable stripe being encoded with an encoding coil.

5. The device of claim 4 further comprising:
    (a) the encoding coil having alternating current;
    (b) the alternating current providing at least one domain reversal in the magnetic strip; and
    (c) a frequency for the current determining a distance between the at least one domain reversal.

6. The device of claim 5 further comprising:
    (a) the alternating current flowing through the coil controlling the intensity of the magnetic field;
    (b) the device being usable in water bath or oil bath suspensions;
    (c) the device being usable with at least one magnetic particle suspension selected from the group consisting of a recirculating unit, an aerosol can, and a portable spraying device; and
    (d) the card having colored or non-white substrate.

7. The device of claim 5 further comprising the device being usable with a dry method material.

8. The device of claim 5 further comprising:
    (a) the magnetic stripe having a code in order to attract particles in a unique pattern of fine lines across the stripe;
    (b) the encoding determining the stripe pattern; and
    (c) a clarity for the stripe pattern illustrating quality of the magnetic inspection particle suspension.

9. The device of claim 5 further comprising:
    (a) the magnetic stripe having a high coercivity application; and
    (b) the magnetic stripe having an oersted capacity of about 3,000 to about 4,000.

10. The device of claim 9 further comprising the magnetic stripe having an oersted capacity of about 3,500 to about 3,800 oersteds.

11. The device of claim 5 further comprising:
    (a) the magnetic stripe having a low coercivity application; and
    (b) the magnetic stripe having an oersted capacity of about 100 to about 400.

12. The device of claim 11 further comprising the magnetic stripe having an oersted capacity of about 250 to about 350.

13. The device of claim 5 further comprising at least two magnetic stripes on the card.

14. A method for determining effectiveness of a magnetic particle suspension comprising:
    (a) providing a card having at least one magnetizable stripe thereon;
    (b) applying a predetermined, magnetic pattern to the at least one magnetizable stripe;
    (c) dipping the magnetic strip into a magnetic particle suspension; and
    (d) observing a pattern of particles on the at least one magnetizable stripe; and
    (e) determining an effectiveness of the magnetic particle suspension.

15. The method of claim 14 further comprising:
    (a) coating the at least one magnetizable stripe with a clear nonmagnetizable coating in order to protect the at least one magnetizable stripe; and
    (b) applying a magnetic gradient to the at least one magnetizable stripe.

16. The method of claim 15 further comprising:
    (a) encoding the at least one magnetizable stripe with alternating current; and
    (b) controlling the intensity of a magnetic field for the at least one magnetizable stripe; and
    (c) using the card in a magnetic inspection system selected from the group consisting of a dry system, a water system and an oil system.

17. The method of claim 16 further comprising:
    (a) providing a used card; and
    (a) wiping the used card in order to permit at least one subsequent use.

18. The method of claim 17 further comprising:
    (a) providing the at least one magnetizable stripe in a reproducible fashion; and
    (b) producing an identical stripe by encoding a second card with the same current.

19. A device for determining effectiveness of a magnetic particle suspension, the device comprising:
    (a) a card having at least one magnetizable stripe thereon;
    (b) a predetermined, magnetized pattern being applied to the at least one magnetizable stripe;
    (c) the predetermined, magnetized pattern being suitable to determine the effectiveness of the magnetic suspension;

(d) the predetermined, magnetized pattern providing at least two different magnetic strength areas to the at least one magnetizable stripe;

(e) a clear nonmagnetizable coating protecting the at least one magnetizable stripe;

(f) the at least one magnetizable stripe being reproducible;

(g) the at least one magnetizable stripe being encoded with an encoding coil;

(h) the encoding coil having alternating current or direct current;

(i) the clear nonmagnetizable coating being at least one coating selected from the group consisting of polyethylene, polypropylene, and mixtures thereof;

(j) the at least one magnetizable stripe having a low magnetic gradient in order to provide improved discrimination as to the magnetic particle suspension;

(k) the at least one magnetizable stripe being duplicatable in order to provide an improved, repeatable, and reproducible test system;

(l) the device failing to display a reading upon loss of magnetism;

(m) the at least one magnetizable stripe having calculatable gradients in order to provide accurate testing;

(n) the at least one magnetizable stripe having verifiable properties;

(o) the alternating current providing at least one domain reversal in the magnetic strip; and (p) a frequency for the current determining a distance between the at least one domain reversal.

20. The device of claim 19 further comprising:

(a) the alternating current flowing through the coil controlling the intensity of the magnetic field;

(b) the device being usable in water bath or oil bath suspensions;

(c) the device being usable with at least one magnetic particle suspension selected from the group consisting of a recirculating unit, an aerosol can, and a portable spraying device;

(d) the card being usable with a suspension selected from the group consisting of a dry method material, an oil based suspension and a water based suspension;

(e) the magnetic stripe having a code in order to attract particles in a unique pattern of fine lines across the stripe;

(f) the encoding determining the stripe pattern; and (g) a clarity for the stripe pattern illustrating quality of the magnetic inspection particle suspension.

\* \* \* \* \*